United States Patent [19]

Fleck et al.

[11] 4,196,229
[45] Apr. 1, 1980

[54] SUBSTITUTED DIVINYL STILBENES AS OPTICAL BRIGHTENERS

[75] Inventors: Fritz Fleck, Bottmingen; Juerg Heller, Allschwil, both of Switzerland

[73] Assignee: Sandoz Ltd., Basel, Switzerland

[21] Appl. No.: 914,403

[22] Filed: Jun. 12, 1978

Related U.S. Application Data

[62] Division of Ser. No. 653,506, Jan. 29, 1976, Pat. No. 4,108,887.

[51] Int. Cl.$^2$ ............................................. C09K 11/06
[52] U.S. Cl. .................................. 427/158; 252/301.21; 427/430.1
[58] Field of Search .......... 260/465 H, 558 R, 558 P, 260/590 D, 607 AR; 252/301.21; 427/158

[56] References Cited

U.S. PATENT DOCUMENTS

| | | | |
|---|---|---|---|
| 3,458,506 | 7/1969 | Bloom et al. | 260/465 H |
| 3,476,747 | 11/1969 | Hargis et al. | 260/465 H |
| 3,629,193 | 12/1971 | Mitzner et al. | 560/81 |
| 3,755,446 | 8/1973 | Scheuermann et al. | 260/559 A |

Primary Examiner—Dolph H. Torrence
Attorney, Agent, or Firm—Gerald D. Sharkin; Richard E. Vila; Thomas C. Doyle

[57] ABSTRACT

Disclosed are compounds of formula I

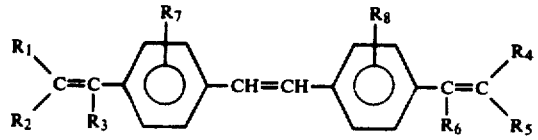

in which $R_1$ and $R_4$, independently, are hydrogen, a non-chromophoric second order substituent, or alkyl or alkenyl unsubstituted or substituted by a non-chromophoric group, $R_2$ and $R_5$, independently, are hydrogen or alkyl or alkenyl, unsubstituted or substituted by a non-chromophoric group, $R_3$ and $R_6$, independently, are hydrogen, alkyl, carboxyl or a non-chromophoric esterified carboxyl group, or $R_2$, together with $R_3$, and/or $R_5$ together with $R_6$, signify an alkylene bridge, $R_7$ and $R_8$, independently, signify hydrogen or a non-chromophoric substituent, or, when $R_7$ is in the 3-position and/or $R_8$ in the 3' position, $R_7$ together with $R_2$, and/or $R_8$ together with $R_5$ signify an alkylene bridge, with the proviso that no more than one of $R_1$ and $R_2$ and no more than one of $R_4$ and $R_5$ signify hydrogen, their production and use as optical brightening agents.

15 Claims, No Drawings

SUBSTITUTED DIVINYL STILBENES AS OPTICAL BRIGHTENERS

This is a division of application Ser. No. 653,506 filed Jan. 29, 1976, now U.S. Pat. No. 4,108,887.

The invention relates to divinyl stilbene derivatives.

The invention provides fluorescent optical brightening agents of formula I,

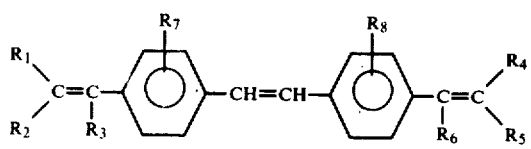

in which $R_1$ and $R_4$, independently, are hydrogen, a non-chromophoric second order substituent, or alkyl or alkenyl unsubstituted or substituted by a non-chromophoric group, $R_2$ and $R_5$, independently, are hydrogen or alkyl or alkenyl, unsubstituted or substituted by a non-chromophoric group, $R_3$ and $R_6$, independently, are hydrogen, alkyl, carboxyl or a non-chromophoric esterified carboxyl group, or $R_2$, together with $R_3$, and/or $R_5$ together with $R_6$, signify an alkylene bridge, $R_7$ and $R_8$, independently, signify hydrogen or a non-chromophoric substituent, or, when $R_7$ is in the 3-position and/or $R_8$ in the 3' position, $R_7$ together with $R_2$, and/or $R_8$ together with $R_5$ signify an alkylene bridge, with the proviso that no more than one of $R_1$ and $R_2$ and no more than one of $R_4$ and $R_5$ signify hydrogen.

Any alkyl in the compounds of formula I is preferably 1 to 6, more preferably of 1 to 4, carbon atoms and any alkenyl is preferably of 2 to 4, more preferably of 2 or 3, carbon atoms. Where $R_2$ and $R_3$, or $R_5$ and $R_6$, together form an alkylene bridge, this is preferably a propylene 1,3 or butylene 1,4 bridge. Where $R_7$ and $R_2$, or $R_8$ and $R_5$, form an alkylene bridge, this is preferably a methylene or ethylene bridge.

By the term "non-chromophoric second order substituent" is meant a substituent which does not confer any colour to the compound as a whole (thereby making it unsuitable as an optical brightening agent) and which has an electron-withdrawing effect. Examples are acyl radicals of carboxylic and sulphonic acids, nitrile and carboxy and sulpho groups and their amides and esters.

The preferred compounds of the invention are the compounds of formula I',

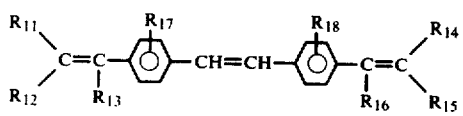

wherein $R_{11}$ and $R_{14}$, independently, are hydrogen; $C_{1-6}$-alkyl, unsubstituted or mono-substituted by $C_{1-4}$alkoxy or $C_{1-4}$alkoxycarbonyl; unsubstituted $C_{2-4}$alkenyl; cyano; trifluoromethyl or a radical

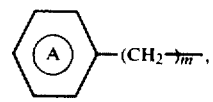

$R_x$—$SO_2$—, $R_x$—CO—, —CO—NR'R'', —$CO_2$R''', $SO_3$M or —$SO_2$NR'R'', $R_{12}$ and $R_{15}$, independently, are hydrogen or $C_{1-6}$alkyl, unsubstituted or mono-substituted by $C_{1-4}$alkoxy or $C_{1-4}$alkoxycarbonyl, $R_{13}$ and $R_{16}$, independently, are hydrogen, unsubsti $C_{1-6}$alkyl or —COOR''', $R_{17}$ and $R_{18}$, independently, are hydrogen, unsubstituted $C_{1-6}$alkyl, cyano, —CONR'R'', —$SO_2(C_{1-4})$alkyl, —$CO_2$R''', —$SO_3$M or —$SO_2$NR'R'', or $R_{12}$ together with $R_{13}$, and/or $R_{15}$ together with $R_{16}$, signify propylene 1,3 or butylene 1,4, or $R_{12}$ together with a 3-position $R_{17}$, and/or $R_{15}$ together with a 3'-position $R_{18}$, signify —$CH_2$— or —$CH_2CH_2$—, $R_x$ signifies methyl; $C_{2-6}$alkyl, unsubstituted or mono-substituted by $C_{1-4}$alkoxy or $C_{1-4}$alkoxy-$C_{2-6}$alkoxy; phenyl, unsubstituted or substituted by up to three substituents selected from up to three selected from $C_{1-3}$alkyl and halogen, up to two from $C_{1-3}$alkoxy and up to one —$SO_3$M group; a radical

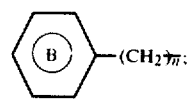

naphthyl or mono-sulphonaphthyl,

R' is hydrogen; methyl; $C_{2-6}$alkyl, unsubstituted or mono-substituted by hydroxy, $C_{1-4}$alkoxy, $C_{2-6}$hydroxyalkoxy, —$SO_3$M or mono- or di-$C_{1-4}$alkylamino; cyclohexyl, unsubstituted or substituted by up to 3 $C_{1-2}$alkyls; phenyl, unsubstituted or substituted by up to three substituents selected from up to three selected from $C_{1-3}$alkyl and halogen, up to two from $C_{1-3}$alkoxy and up to one —$SO_3$M groups; or a radical

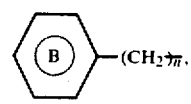

R'' is hydrogen; methyl; $C_{2-6}$alkyl, unsubstituted or mono-substituted by hydroxy, $C_{1-4}$alkoxy or $C_{2-6}$hydroxyalkoxy, R''' is M; methyl; $C_{2-6}$alkyl, unsubstituted or mono-substituted by hydroxy, $C_{1-4}$alkoxy, $C_{1-4}$alkoxy-$C_{2-6}$alkoxy, $C_{2-6}$hydroxyalkoxy; cyclohexyl, unsubstituted or substituted by up to 3 $C_{1-2}$alkyls; phenyl, unsubstituted or substituted by up to three substituents selected from up to three selected from $C_{1-3}$alkyl and halogen, up to two from $C_{1-3}$alkoxy and up to one —$SO_3$M group; a radical

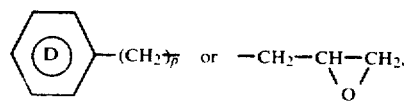

m is 1 or 2,
n and p, independently, are 1 or 2,
M is hydrogen or a non-chromophoric cation, and
rings A, B and D, independently, are unsubstituted or substituted by up to three substituents selected from up to two from $C_{1-3}$alkyl and up to two from halogen.

In the compounds of formula I', any halogen is preferably chlorine.

$R_{11}$ and $R_{14}$, independently, preferably signify $C_{2-4}$alkenyl, CN, —CONR'R", —COOR''', —SO$_2$NR'R", Rx—SO$_2$— or Rx—CO—, more preferably the latter six groups and especially —CN, —COOR''' and Rx—SO$_2$—.

$R_{12}$ and $R_{15}$, independently, preferably signify unsubstituted $C_{1-4}$alkyl (preferably methyl) or hydrogen, more preferably hydrogen.

$R_{13}$ and $R_{16}$, independently, preferably signify hydrogen or $C_{1-4}$alkyl, more preferably hydrogen or methyl.

$R_{17}$ and $R_{18}$, where other than hydrogen or forming alkylene bridges, are preferably in positions 2 and 2', their preferred significances being hydrogen and —SO$_3$M, particularly hydrogen.

Rx is preferably methyl, $C_{2-6}$alkyl, unsubstituted or mono-substituted by $C_{1-4}$alkoxy or by $C_{1-4}$alkoxy-$C_{2-6}$alkoxy; phenyl, unsubstituted or mono-substituted by halogen (preferably chlorine), $C_{1-3}$alkyl or $C_{1-3}$alkoxy; or naphthyl; more preferably unsubstituted $C_{1-6}$alkyl (of which $C_{1-4}$alkyl and methyl are particularly preferred) and phenyl, unsubstituted or mono-substituted by chlorine or methyl.

R' is preferably hydrogen, methyl, $C_{2-4}$alkyl, unsubstituted or mono-substituted by hydroxy, more preferably hydrogen.

R" is preferably hydrogen, methyl or $C_{2-4}$alkyl, unsubstituted or mono-substituted by hydroxy, more preferably hydrogen.

R' and R" preferably have the same significance.

R''' is preferably methyl or $C_{2-6}$alkyl mono-substituted by hydroxy, $C_{1-4}$alkoxy, $C_{1-4}$alkoxy-$C_{2-6}$alkoxy or $C_{2-6}$hydroxyalkoxy, more preferably unsubstituted $C_{1-6}$alkyl, of which $C_{1-4}$alkyl and particularly methyl are especially preferred.

m, n and p are preferably 1.

Where M is a cation, the exact nature thereof, provided it is non-chromophoric, is not critical and may be any cation conventional in the optical brightener art, e.g. an alkali-metal cation such as of lithium, sodium or potassium, preferably sodium, an alkaline earth metal cation or an ammonium, alkylammonium or substituted alkylammonium cation, e.g. of formula RpRqRsN⊕H where Rp, Rq and Rs, independently, are hydrogen, unsubstituted $C_{1-4}$alkyl or $C_{2-4}$alkyl substituted, preferably once, by hydroxy, e.g. mono-, di- or tri-ethanolammonium and mono-, di- and tri-isopropanolammonium.

As a more preferred class of compounds may be given the compounds of formula I",

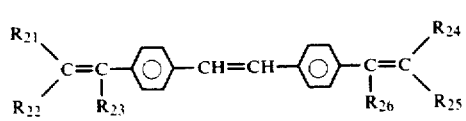

in which
$R_{21}$ and $R_{24}$, independently, are $C_{2-4}$alkenyl, —CN, —CONR'R", —COOR''', Rx—SO$_2$— or Rx—CO—, where R', R", R''' and Rx and the preferred and more preferred significances thereof are as defined above, and
$R_{22}$, $R_{23}$, $R_{25}$ and $R_{26}$, independently, are hydrogen or unsubstituted $C_{1-4}$alkyl.

In the compounds of formula I" at least one of $R_{22}$ and $R_{23}$ and at least one of $R_{25}$ and $R_{26}$ preferably signify hydrogen. More preferably all four signify hydrogen.

Particularly preferred compounds of the invention are the compounds of formula I''',

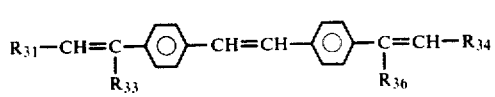

in which
$R_{31}$ and $R_{34}$, independently, signify —CN, —COOR''' or —SO$_2$—Rx, where R''' and Rx and the preferred and more preferred significances thereof are as defined above,
$R_{33}$ and $R_{36}$, independently, signify hydrogen or $C_{1-4}$alkyl, preferably both being hydrogen.

The most preferred class of compounds provided by the invention is the class of formula $I^{iv}$,

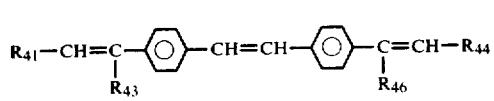

wherein
$R_{41}$ and $R_{44}$, independently, signify —CN, —COOR$^{iv}$ or —SO$_2$Rx$^{iv}$, preferably the latter two, where R$^{iv}$ is methyl or $C_{2-6}$alkyl, unsubstituted or mono-substituted by hydroxy, $C_{1-4}$alkoxy, $C_{1-4}$alkoxy-$C_{2-6}$alkoxy or $C_{2-6}$hydroxyalkoxy; preferably unsubstituted $C_{1-4}$alkyl, Rx$^{iv}$ is unsubstituted $C_{1-6}$alkyl or phenyl, unsubstituted or mono-substituted by halogen (preferably chlorine), $C_{1-3}$alkyl or $C_{1-3}$alkoxy; preferably unsubstituted $C_{1-4}$alkyl or phenyl, unsubstituted or mono-substituted by chlorine, methyl or methoxy, and
$R_{43}$ and $R_{46}$, independently, are hydrogen or methyl, preferably both being hydrogen.

All the compounds provided by the invention, whether of formula I, I', I", I''' or $I^{iv}$, are preferably symmetrical.

The invention also provides a process for the production of compounds of formula I, characterised by
(a) reacting a compound of formula II,

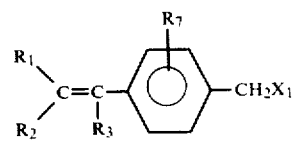

where $X_1$ is hydrogen, —COOM, —ZnBr, —ZnCl, —MgBr, —MgCl, or a radical

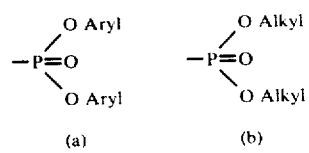

(a)        (b)

-continued

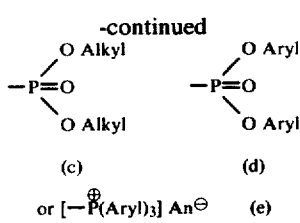

(c)      (d)

or $[-\overset{\oplus}{P}(Aryl)_3]\, An^{\ominus}$    (e)

with a compound of formula III,

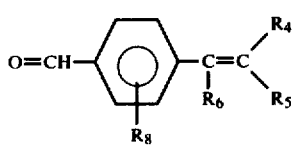

or a functional derivative thereof, (b) obtaining a symmetrical compound of formula I by reacting a compound of formula IV,

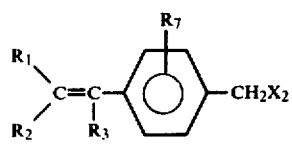

with a compound of formula V,

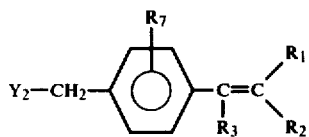

where $X_2$ and $Y_2$ are halogen, e.g. chlorine, bromine or iodine, preferably chlorine, in the presence of a condensation agent, preferably an alkali alcoholate, (c) obtaining a symmetrical compound of formula I and in which the stilbene phenylene groups are unsubstituted, by reducing a compound of formula VI

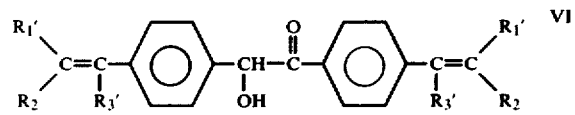

wherein $R_1'$ and $R_3'$ have the same significances as $R_1$ and $R_3$, other than ester groups, and any carboxy or sulpho group is in alkali-metal salt form and, where required, esterifying any acid groups as $R_1'$ and $R_3'$ and converting any carboxy or sulpho group in alkali-metal salt form into the free acid or other salt form, (d) obtaining a compound of formula I in which $R_2$ does not form a bridge with $R_3$ or $R_7$, and $R_5$ does not form a bridge with $R_6$ or $R_8$, by reacting a compound of formula VII

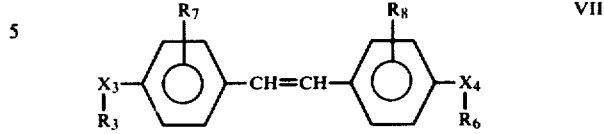

with a compound of formula VIII

and with a compound of formula IX

one of $X_3$ and $Y_3$ and one of $X_4$ and $Y_4$ signifying a carbonyl group or a functional derivative thereof, the other signifying

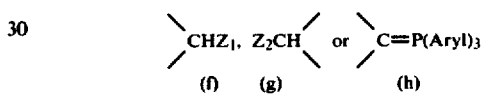

(f)    (g)    (h)

where $Z_1$ and $Z_2$ signify $-ZnBr$, $-ZnCl$, $-MgBr$, $-MgCl$ or a radical (a), (b), (c), (d), or (e), above, with proviso that at least one of the substituents bound to radical (f) or (g) is a second order substituent when $Z_1$ or $Z_2$ is other than a radical (e), (e) obtaining a symmetrical compound of formula I, which is free from carboxylic acid aryl ester groups, by heating a compound of formula X

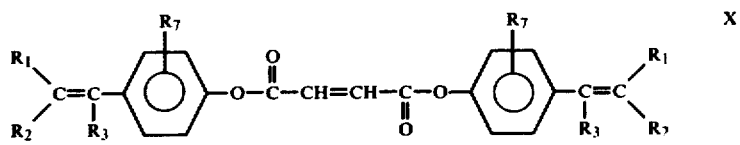

wherein the radicals $R_1$, $R_2$, $R_3$ and $R_7$ are as defined above but do not signify nor contain carboxylic acid aryl ester groups.

As will be appreciated, interconversions from one compound of formula I to another, may also be carried out, e.g. carboxylic acid groups converted into ester groups. Further, any sulpho or carboxylic acid group obtained in salt form may be converted into the free acid form or vice versa in conventional manner, as can conversion of one salt form into another.

The above processes (a) to (e) may be carried out in conventional manner, as described in the literature.

Special embodiments of process (d) consist in producing compounds of formula I, wherein $R_1$ and $R_4$ signify the carboxy group or a carboxylic acid ester group, $R_2$ and $R_5$ signify hydrogen and $R_3$ and $R_6$ signify hydrogen or alkyl, such that the corresponding aldehyde or the ketone of formula VII is reacted with malonic acid, e.g. under the conditions in the Knoevenagel-Döbner reaction, whereby the monocarboxylic acid is obtained with decarboxylation, and this may subsequently be optionally esterified to form the corresponding esters, or, in order to produce these esters, a reaction is made directly with malonic acid monoalkyl ester, or in order to produce the corresponding compounds wherein R₁ and R₄ signify the cyano group, the corresponding aldehyde or the ketone of formula VII is reacted with cyanoacetic acid, whereupon the monocyano compound obtained may be reacted to form the corresponding ester by reaction with a corresponding alcohol and with sulphuric acid or hydrogen chloride.

The compounds of formula VI are suitably obtained by treatment of compounds XI

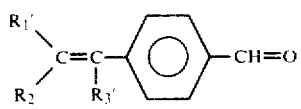  XI with cyanide ions, again in conventional manner.

The compounds of formulae II, III, IV, V, and VII to XI are either known or may be obtained from available starting materials in manner analogous to known compounds.

The resulting compounds of formula I may be isolated and purified in conventional manner.

The compounds of the invention are fluorescent optical brightening agents suitable for brightening a wide variety of natural, semi-synthetic and synthetic materials.

Those compounds of the invention containing sulpho groups are useful for the brightening of substrates brightenable using anionic optical brighteners, e.g. natural or regenerated cellulose, natural or synthetic polyamides and polyurethanes.

The compounds of the invention free from sulpho groups, and which are preferably also free from —COOM groups, are useful for brightening semi-synthetic or fully synthetic high molecular weight polymers, e.g. polyesters, polyamides, polyurethanes, polypropylene and cellulose esters and, particularly when they contain basic amino groups, also polyacrylonitrile.

The substrate to be brightened may be in any desired form, e.g. yarn, thread, filament, woven, knitted, semi-finished or finished form. The application of the compounds of the invention may be carried out in conventional manner, e.g. employing the exhaust, steeping or padding techniques, from aqueous baths, optionally containing carriers, thickeners and dispersing agents, followed by fixation, e.g. using saturated steam, high temperature treatments or the thermosol method.

The compounds of the invention free from sulpho groups are also suitable for the brightening of organic materials in the mass, e.g. by addition to melts, solutions or monomers or prepolymers. When brightening polyester, preferably polyglycol terephthalate, in the mass, the compounds may be used in the powder process but are preferably incorporated into the polymer by addition before or during poly-condensation. The compounds of formula I''', wherein R₃₁ or R₃₄ signifies —CN or —COOR''' may be condensed into the polyester chain, thereby giving particularly favourable wash- and light-fastness.

The compounds of the invention free from sulpho groups are also well absorbed onto polyester substrates without the use of a carrier.

The concentration of brightener in relation to the substrate being brightened falls within the usual range, e.g. between 0.001 and 0.5%, preferably between 0.01 and 0.2%, based on the weight of the substrate, depending on the material to be brightened and the method of application. The brighteners of the invention, especially those of formulae I'' to I^iv have good resistance to storage and heat and give red to bluish hues with high maximum whiteness values and good all-round fastness properties.

The bluish fluorescent optical brightening agents of the invention, especially those wherein R₂, R₃, R₅ and R₆, and preferably also R₇ and R₈, all signify hydrogen, and R₁ or R₄, preferably both, signify second order substituents, especially non-hydro-solubilising such substituents, are useful for use in combination with compatible decidedly reddish hued brighteners, e.g. of the naphthalimide or bis-benzoxazolyl-ethylene series such as described in French Pat. Nos. 1,146,161; 1,168,227 and 1,344,883, in German Published Specification Nos. 2,147,706 and 2,231,609, and in Japanese Patent Application Publication No. 71-05596. These combinations give particularly brilliant brightening effects with high maximum whiteness values which are believed to result from a synergistic effect. Such combinations preferably contain from 5 to 90%, more preferably from 5 to 50%, by weight of the bluish brightener of the present invention. These combinations may be used as described above.

With the brighteners of the invention and with the above described combinations, free from hydro-solubilising groups, aqueous dispersions containing 5 to 20% of brightener and conventional dispersing agents and optionally further assistants may be obtained.

The compounds of the invention containing —COOM groups are particularly fluorescent and are especially suitable as intermediates for producing the corresponding ester group containing compounds of the invention.

The following Examples, in which all parts and percentages are by weight and all temperatures in degrees centigrade, illustrate the invention.

EXAMPLE 1

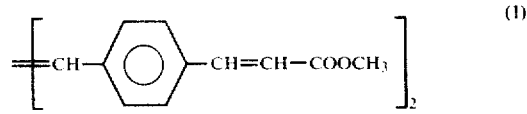  (1)

118 parts of stilbene-4,4'-dialdehyde [see Chem. Ber. 91, p. 1276 (1958)] and 150 parts of anhydrous malonic acid are heated with stirring for 16 hours at reflux in 500 parts of dry pyridine and 1 part of piperidine until boiling. The reaction mixture is discharged into 3000 parts of water, the carboxylic acid (2) is suctioned off, washed with diluted hydrochloric acid, water and methanol and dried in a vacuum.

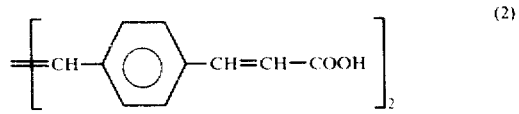  (2)

100 parts of the acid (2) are boiled at reflux for 3 hours in 300 parts of thionyl chloride. The acid goes into solution with a strong development of SO₂ and HCl.

The excess thionyl chloride is distilled off, at the end in a vacuum. The residue of the dicarboxylic acid chloride (3)

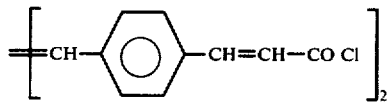

is boiled at reflux in 2000 parts of absolute methyl alcohol until the hydrogen chloride ceases to be produced. The methyl ester (1) which is separated in the cold is filtered off and recrystallised from chlorobenzene. Melting point 268°–270°, green-irridescent yellow flakes.

EXAMPLE 2

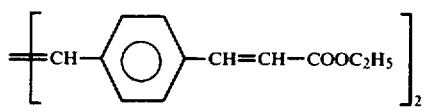

100 parts of stilbene-4,4'-dialdehyde are heated with stirring at reflux with 150 parts of malonic acid monoethylester and 500 parts of dry pyridine and 0.5 parts of piperidine until the aldehyde has disappeared in the thin-layer chromatograph. Purification is carried out by recrystallisation from hydrocarbon mixture which boils at between 150° and 180°; melting point 240°–249°.

EXAMPLE 3

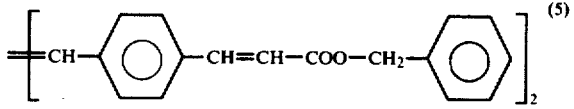

100 parts of the methyl ester (1) are heated to 160°–180° in 1000 parts of benzyl alcohol, in which 5 parts of sodium have been dissolved, in a distillation apparatus with methanol being distilled off, until the initial product has disappeared in the thin-layer chromatograph. The benzyl ester (5) is recrystallised from o-dichlorobenzene to give greenish-yellow flakes.

EXAMPLE 4

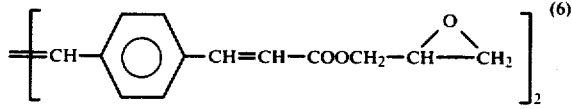

By heating 100 parts of methyl ester (1) with 1000 parts of glycidol and 5 parts of sodium as described in example 3, the compound (6) is obtained as greenish-yellow flakes.

EXAMPLE 5

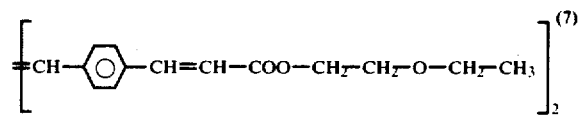

100 parts of stilbene-4,4'-dialdehyde are dissolved with heating in 1700 parts of dimethyl formamide. 330 parts of ethoxyethoxycarbonylmethyldiethyl phosphonate of formula (8)

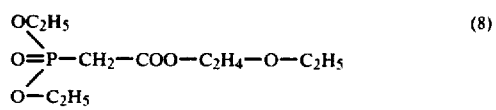

are added to the cooled solution and a solution of 24 parts of sodium in 300 parts of anhydrous ethylene glycol monoethylether is added in drops with vigorous stirring at room temperature. The ester (7) immediately begins to recrystallise from the red solution. After stirring for 5 hours at 20°–30°, the mixture is neutralised by adding acetic acid, 500 parts of water are added and the deposit is suctioned off. The dried compound (7) melts after recrystallisation twice from chlorobenzene at 257°–259° it is in the form of green-irridescent yellow flakes. The solutions in chlorobenzene fluoresce in an intense violet-blue shade. The phosphonate (8) is produced as follows:

250 parts of monochloro acetic acid are esterified by heating in 1500 parts of ethylene glycol monoethylether, with dry hydrogen chloride being passed through. The ester boils at 12 tor at 87°–91°. 330 parts of the chloroacetic acid ester are heated with 400 parts of triethyl phosphite gradually to 140°, until the ethyl chloride has been formed, and then distilled in a vacuum. Boiling point 168°–172°.

Similarly, the methoxy ethylester (9) is obtained from the methoxy ethyl ester of the chloroacetic acid.

EXAMPLE 6

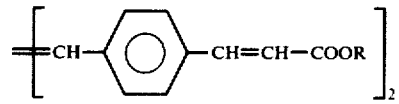

The esters listed in the following table may be produced in a manner similar to that described in examples 1–5.

The esters are recrystallised from chlorobenzene or a hydrocarbon mixture which boils at 150°–180°.

| Compound | similar to ex. | R | Fluorescence in chlorobenzene |
|---|---|---|---|
| (4) | 5 | —CH₂—CH₃ | violet-blue |
| (7) | 3 | —CH₂—CH₂—O—CH₂—CH₃ | " |
| (9) | 3 | —CH₂—CH₂—O—CH₃ | " |
| (10) | 5 | —CH₂—CH₂—CH₃ | " |
| (11) | 5 | —CH(CH₃)₂ | " |
| (12) | 2 | —CH₂—CH₂—CH₂—CH₃ | " |
| (13) | 5 | —(CH₂)₄—CH₃ | " |

-continued

| Compound | similar to ex. | R | Fluorescence in chlorobenzene |
|---|---|---|---|
| (14) | 1 | —⟨C₆H₅⟩—H | " |
| (15) | 5 | —C₂H₄—O—C₂H₄—O—C₂H₅ | " |
| (16) | 3 | —C₂H₄—O—C₂H₄—O—CH₃ | " |

EXAMPLE 7

20 parts of powdered sodium and 100 parts of stilbene-4,4′-dialdehyde are entered with ice cooling into 600 parts of alcohol-free ethyl acetate, the mixture is stirred for 16 hours at room temperature, it is neutralised with glacial acetic acid, 600 parts of water are added, the ester (4) formed is filtered off and is purified by recrystallisation from toluene.

EXAMPLE 8

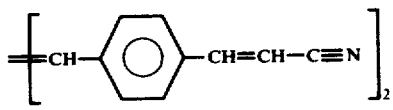
(17)

100 parts of stilbene-4,4′-dialdehyde and 200 parts of cyanomethyl diethyl phosphonate (18)

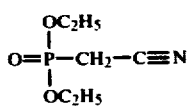
(18)

are dissolved in 1500 parts of dimethyl formamide and a solution of 24 parts of sodium in 300 parts of absolute alcohol is added drop-wise with stirring at 20°–30°. After the solution has been standing for 16 hours, it is neutralised with glacial acetic acid, the cyano compound (17) is precipitated with 1500 parts of water and it is recrystallised from butyl alcohol. The phosphonate (18) is obtained by heating 400 parts of acetonitrile with 1000 parts of triethyl phosphite for 5 hours at 100°, and distilling in a vacuum.

EXAMPLE 9

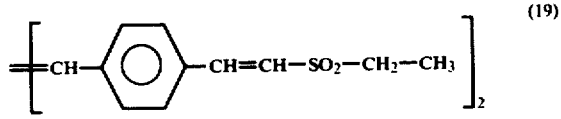
(19)

Instead of using the 200 parts of cyanomethyl diethyl phosphonate (18) in example 8, by using 340 parts of ethyl sulphonylmethyldiethyl phosphonate (20)

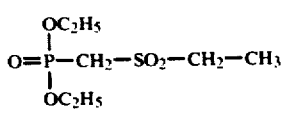
(20)

and otherwise using the same procedure, the sulphone (19) is obtained in good yield. The compound is fluorescent in an intense violet-blue shade and is particularly suitable as a brightener for polyester-spun fabric.

The production of the diethyl sulphonyl methylphosphonate (20) is described in Zh. Obshch. Khim. 27, 2360 (1957).

EXAMPLE 10

The brighteners 21–29 of formula

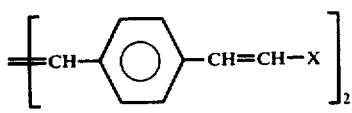
(21–32)

are prepared employing the phosphonates

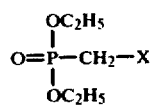

by the Horner variation of the Wittig reaction [see Chem. Ber. 95, 581 (1962)], see also Synthesis 1975 (4), 278.

| Brightener | X | Fluorescence in chlorobenzene |
|---|---|---|
| (21) | —SO₂—CH₃ | violet-blue |
| (22) | —SO₂—⟨C₆H₅⟩ | " |
| (23) | —SO₂—⟨C₆H₄⟩—Cl | " |
| (24) | —SO₂—⟨C₆H₄⟩—CH₃ | " |
| (25) | —SO₂—⟨naphthyl⟩ | " |
| (26) | —CO—NH₂ | " |
| (27) | —CO—N(CH₃)₂ | " |
| (28) | —CO—NH—(CH₂)₃—N(CH₃)₂ | " |
| (29) | —CO—NH—(CH₂)₃—N(C₂H₅)₂ | " |
| (30) | —CO—NH—⟨C₆H₄⟩—SO₃Na | " |

-continued

| Brightener | X | Fluorescence in chlorobenzene |
|---|---|---|
| (31) | —CO—N(CH₃)—CH₂—CH₂—SO₃Na | " |
| (32) | —CO—N(CH₂—CH₂—OH)(CH₂—CH₂—OH) | " |

The brighteners (30) to (32), as well as (26) to (29) stem from the acid chloride (3) of example 1 or an ester such as (1) or (4) by heating it with ammonia or the corresponding amines.

The brighteners (30) and (31) containing sulpho groups are polyamide brighteners, the compounds (28) and (29) are suitable polyacrylonitrile brighteners.

EXAMPLE 11

183 parts of the 4,4'-bis-bromomethyl stilbene produced in accordance with Chem. Ber. 91, 1278 (1958) are heated gradually to 150° with 216 parts of triethyl phosphite in a stirring apparatus having a decreasing cooler, the ethylene bromide thus formed being distilled off, and the excess triethyl phosphite is distilled off in a partial vacuum. The residue is absorbed in 3000 parts of dimethyl formamide, a solution of 29 parts of sodium in 500 parts of absolute ethanol and subsequently 140 parts of glyoxalic acid ethyl ester in 140 parts of absolute ethyl alcohol is slowly added in drops. The mixture is stirred for 20 hours, neutralised to a pH of 7 with glacial acetic acid and the ester (4) is precipitated by dilution with 3000 parts of water, suctioned off, washed with water and alcohol and dried. The brightener is identical with that synthesised in example 2. The same compound may also be obtained by heating 100 parts of the brightener (17) in 2000 parts of absolute alcohol which is saturated by hydrogen chloride for 10 hours at reflux.

EXAMPLE 12

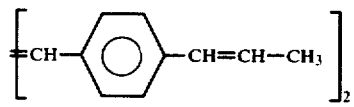

(33)

118 parts of stilbene-4,4'dialdehyde (example 1) and 482 parts of triphenylethyl phosphonium bromide produced by the Wittig method [Ann. der Chem. 606, 1 (1957)] are dissolved together with heating in 2000 parts of dimethyl formamide, and a solution of 28 parts of sodium in 600 parts of absolute ethyl alcohol is slowly added drop-wise to the cooled mixture. This is stirred for 5 hours at 60°, the reaction mixture is poured into cold water, the resultant deposit is filtered off, the filtration residue is washed and dried, and the olefin (33) is isolated therefrom by extraction with ether in which the resultant triphenyl phosphine oxide is insoluble. (33) dissolves in chlorobenzene with a violet fluorescence.

Instead of the 482 parts of triphenylethyl phosphonium bromide, by using 500 parts of triphenylallyl phosphonium bromide [Chem. Ber. 87, 1229 (1954)] or triphenyl-methallyl phosphonium bromide, in the same procedure, the brighteners (34) and (35) are obtained,

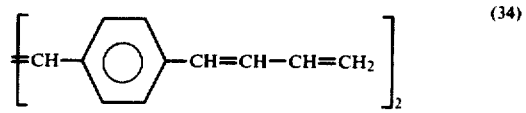

(34)

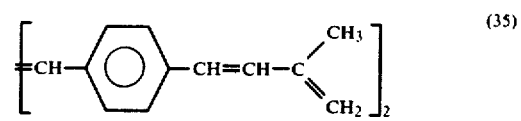

(35)

which in chlorobenzene have an intense blue fluorescence.

EXAMPLE 13

118 parts of stilbene dialdehyde-(4,4') are boiled at reflux in 5000 parts of boiling toluene in a nitrogen atmosphere for 14 hours, with 350 parts of the compound of formula (36)

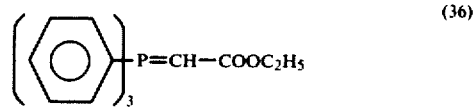

(36)

which is produced in accordance with Helv. Chimica Acta 40, 1247 (1957). From the concentrated reaction mixture, a mixture of the ester of formula (4) with triphenyl phosphine oxide, is crystallised in the cold, from which the brightener is isolated by extraction with ether.

By replacing the phosphorane (36) with the phosphorane of formula (37)

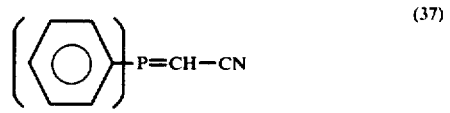

(37)

which is described in Chem. Ber. 94, 578 (1961), under the same conditions, the compound of formula (17) of example 8 is obtained.

EXAMPLE 14

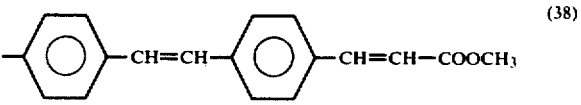

(38)

135 parts of p-bromomethyl cinnamic acid ethyl ester (produced by bromination of p-methyl cinnamic acid ethyl ester with bromosuccinimide in carbon tetrachloride) are heated to 100°-120° in a distillation apparatus with 100 parts of triethyl phosphite, whereby ethyl bromide is distilled off. It is then reheated for 2 hours and the excess triethyl phosphite is distilled off in a partial vacuum. The residue of the phosphonate of formula (39)

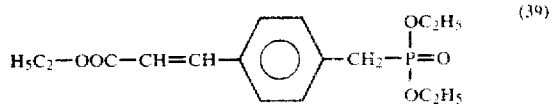

is dissolved in a stirring apparatus in 2000 parts of dimethyl formamide, 95 parts of p-formyl-cinnamic acid methyl ester are added [see Chem. Ber. 34, 2784 (1901)]. A solution of 14 parts of sodium in 200 parts of methyl alcohol is added slowly in drops at 20°–30° to the solution, and the mixture is stirred for 16 hours. Precipitation of compound (38) is completed by adding 2000 parts of water, the product is filtered off, washed with water and methanol, vacuum dried and recrystallised from hydrocarbon mixture having a boiling point of 150°–180°. Green-irridescent yellow flakes which dissolve in most solvents with intensive violet-blue fluorescence, are produced.

The compound (4) of example 2 is obtained similarly employing 100 parts of p-formyl cinnamic acid ethyl ester.

EXAMPLE 15

112 parts of p-chloromethyl cinnamic acid methylester (produced by chlorination of p-methyl cinnamic acid ethylester with N-chlorosuccinimide in the presence of benzyl peroxide in carbon tetrachloride) are entered slowly with stirring in small portions into a solution of 55 parts of potassium-tert.-butylate in 1500 parts of dimethyl sulphoxide at room temperature. The mixture is stirred until the red dye disappears and is discharged into water. From the precipitate, the compound of formula (4) is isolated by recrystallisation.

EXAMPLE 16

99 parts of the Na-salt of p-formyl cinnamic acid are heated at reflux for 5 hours with 1000 parts of alcohol and 44 parts of potassium cyanide in 1000 parts of water. The product is precipitated in water and hydrochloric acid at a pH of 2–3, and suctioned off. The crude benzoin-4,4′-diacrylic acid is heated at reflux in 5000 parts of glacial acetic acid with 150 parts of stannous chloride and 750 parts of concentrated hydrochloric acid, for 5 hours. The precipitated deoxybenzoindiacrylic acid is filtered off, dried and converted into the acid chloride by heating in 250 parts of thionyl chloride, and this is converted into the isopropyl ester by boiling for 2 hours in 1200 parts of isopropyl alcohol. The cold filtered and dried ester is then mixed intimately with 80 parts of aluminium isopropylate and is then heated at 180°–200° while the acetone is distilled off and then at 250°, until the deoxybenzoin ester has disappeared in the thin-layer chromatograph. The ester obtained is identical with compound (11) in example 6.

EXAMPLE 17

The brighteners of the table below may be produced as in example 5, employing appropriate starting materials:

$$\left[=CH-\underset{}{\bigcirc}-\underset{R_3}{\overset{R_1}{C=C}}\underset{R_2}{\diagdown}\right]_2$$

| Brightener | $R_1$ | $R_2$ | $R_3$ | Fluorescence |
|---|---|---|---|---|
| 40 | —COOC$_2$H$_5$ | —CH$_3$ | H | violet |
| 41 | —CN | —CH$_3$ | H | violet |
| 42 | —COOCH$_3$ | —H | —CH$_3$ | blue-violet |
| 43 | —CN | —H | —CH$_3$ | blue-violet |
| 44 | —CO—CH$_3$ | H | H | blue-violet |
| 45 | —CO—CH$_3$ | —CH$_3$ | H | blue-violet |

APPLICATION EXAMPLE A

A fabric of polyethylene glycol terephthalate is treated for 30 minutes at the boil at a liquor ratio of 1:40 with 0.2% of compound (1) of Example 1 in the form of an aqueous dispersion. The compound (I) having been admixed with a dispersion agent based on dinaphthyl methane disulphonic acid and ground therewith in a sand mill, prior to production of the aqueoue dispersion. The fabric thus treated, after rinsing and drying, shows a brilliant, neutral to bluish white shade. Similar brightening may be obtained by using the compound (4) of example 2 or the compound (7) or (9) to (16) of example 6 in the same manner.

By adding to the bath 2 g per liter of trichlorobenzene as the carrier, a considerably better whitening effect is obtained, with otherwise the same treatment.

Instead of the compound (4), by using a mixture of 50% bis-[5-methylbenzoxazolyl]-ethylene and 50% of compound (4), a brilliant neutral brightening is obtained, which is considerably lighter than that obtained using the same amount of the bisbenzoxazole brightener.

APPLICATION EXAMPLE B 0.6 ml of acetic acid 4% and 0.06 g of oleyl sulphonate are added to 100 ml of water. A solution of the brightener (1) of Example 1 is produced, by dissolving 1 g thereof in 1000 ml ethylene glycol monoethyl ether. 6 ml of this stock solution is added to the above-described aqueous solution, which is heated to 60°. Then, a triacetate-twill fabric weighing 3 g is added to the solution. The temperature is increased over the course of 10 minutes to 95°–98° and the fabric is left at this temperature for 30 minutes. It is then rinsed and dried. The fabric thus treated is considerably brighter than the initial material.

A similar brightening effect is obtained with the brighteners (4) to (16). A polyamide staple fabric is also considerably brightened by the same method by brighteners 26, 27, 30–33.

APPLICATION EXAMPLE C

A polyethylene glycol terephthalate fabric weighing 15 g is added to a treatment bath containing 3 g of a 10% dispersion of the brightener (11) of example 6 in 297 g of water, this brightener being disperse with the aid of dioctylphenyl decaglycolether oxyacetic acid sodium salt. The bath is heated to 130° over the course of 60 minutes in a pressure apparatus, rinsed cold and dried. The fabric thus treated is considerably brighter than the untreated initial material. A similar improvement in the degree of whiteness is obtained on a polypropylene fabric using a dispersion of the brightener (6) of Example 4.

APPLICATION EXAMPLE D

A fabric of polyethylene terephthalate fibres is treated at room temperature on a dye padder with an aqueous dispersion containing per liter 0.5 g of compound (7) of example 6 and 1 g of an addition product consisting of about 8 mols of ethylene oxide on 1 mol of p-tert.-octylphenol. It is squeezed out to 80% liquid absorption, dried for 30 minutes at 60° and subsequently subjected to heat treatment for 1 minute at 200°. The material thus treated has a good bluish, considerably whiter appearance than the untreated material. Instead of polyester fabric, by using a mixed fabric of polyester with cotton (50:50) and using compound (10) of example 6 instead of compound (7), a considerably whiter material than the untreated fabric is also obtained. By using 0.05 g of (7) and 0.35 g of 4,5-diethoxynaphthalic acid methylimide instead of 0.5 g of (7), a very brilliant neutral brightening effect is obtained, which appears much whiter than with the naphthalimide brightener alone.

APPLICATION EXAMPLE E 50 parts of polyester fabric are covered for a short time by a mixture of 250 parts by volume of trichloroethylene and 250 parts by volume of chlorobenzene, in which 0.2 parts of brightener (7) of example 5 are dissolved. The excess solvent is hydro-extracted (about 100% solvent absorption) and the fabric is vacuum dried at 60°, and subsequently treated for 15 minutes with water vapour at 120°-130°. The polyester fabric shows a higher degree of whiteness than a fabric which is similarly subjected to chemical purification without the addition of the brightener. A similar improvement in the degree of whiteness is obtained with the compound (17) of example 8.

APPLICATION EXAMPLE F 0.2 ml of formic acid 85% and 0.06 g of dioctylphenyl decaglycolether are added to 100 ml of water. 30 ml of a 0.1% solution of the brightener (28) of example 10 in ethylene glycol monoethylether is added, the bath is heated to 60° and 3 g of a polyacrylonitrile fabric is added. The temperature is increased to 100° and the fabric is left for 45 minutes at this temperature. It is then rinsed and dried. The fabric thus treated has a considerably whiter and more brilliant appearance than the untreated fabric. A similar brightening effect is obtained with compound (29) of example 10.

APPLICATION EXAMPLE G 200 parts of polyethylene glycol terephthalate are melted in a container in a nitrogen atmosphere at 280° and 0.04 parts of the compound (17), (19), (21) or (24) are added. The brightening agent melts at this temperature and is stirred into the polyester until there is a homogeneous solution. 4 parts of titanium dioxide are then added as a dulling agent and the entire mass is stirred again until a homogeneous mixture is obtained. The matter is then pressed through a spinneret and the thread produced is firstly cooled in a jet of water and then stretched and wound onto spools in the usual manner.

Products produced from these fibre materials have a considerably whiter shade than those produced by the same process, but without the addition of the brightening agent.

By using instead of the compounds (17), (19), (21) or (24), another of the compounds of example 6, similar whitening effects are obtained.

APPLICATION EXAMPLE H 100 parts of a polyvinyl chloride mass consisting of 65 parts of polyvinyl chloride, 35 parts of a softener, e.g. dioctylphthalate and 2%, based on the polymer, of a stabilizer, are mixed with 0.05 parts of the brightener obtained in accordance with examples 1, 2, 3 or 6, they are processed for 10 minutes at 150°-160° on a rolling mill and stretched into sheets. In order to produce opaque sheets, 2.5% titanium dioxide are mixed with the mass before processing. The sheets thus produced have an improved appearance, compared with those produced similarly without brighteners.

What is claimed is:

1. A process for optically brightening a synthetic or semi-synthetic high molecular weight organic material which comprises applying thereto an effective amount of a compound of the formula:

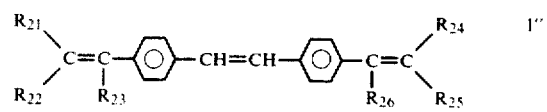

in which $R_{21}$ and $R_{24}$, independently, are $C_{2-4}$alkenyl, —CN, —CONR'R", —COOR''', Rx—SO$_2$— or Rx—CO—, $R_{22}$, $R_{23}$, $R_{25}$ and $R_{26}$, independently, are hydrogen or unsubstituted $C_{1-4}$alkyl, Rx signifies methyl; $C_{2-6}$alkyl, unsubstituted or monosubstituted by $C_{1-4}$alkoxy or $C_{1-4}$alkoxy-$C_{2-6}$alkoxy; phenyl, unsubstituted or substituted by up to three substituents selected from up to three selected from $C_{1-3}$alkyl and halogen and up to two from $C_{1-3}$-alkoxy; a radical

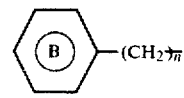

or naphthyl,

R' is hydrogen; methyl; $C_{2-6}$alkyl, unsubstituted or mono-substituted by hydroxy, $C_{1-4}$alkoxy, $C_{2-6}$hydroxyalkoxy, or mono -or di-$C_{1-4}$alkylamino; cyclohexyl, unsubstituted or substituted by up to 3 $C_{1-2}$alkyls; phenyl, unsubstituted or substituted by up to three substituents selected from up to three selected from $C_{1-3}$alkyl and halogen and up to two from $C_{1-3}$alkoxy; or a radical

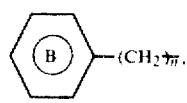

R" is hydrogen; methyl; $C_{2-6}$alkyl, unsubstituted or mono-substituted by hydroxy, $C_{1-4}$alkoxy or $C_{2-6}$hydroxyalkoxy, R''' is M; methyl; $C_{2-6}$alkyl, unsubstituted or mono-substituted by hydroxy, $C_{1-4}$alkoxy, $C_{1-4}$alkoxy-$C_{2-6}$-alkoxy or $C_{2-6}$hydroxyalkoxy; cyclohexyl, unsubstituted or substituted by up to 3 C$_{1-2}$alkyls; phenyl, unsubstituted or substituted by up to three substituents selected from up to three selected from C$_{1-3}$alkyl and halogen and up to two from C$_{1-3}$-alkoxy; or a radical

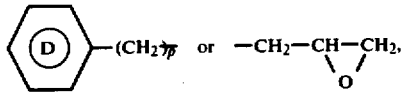

n and p, independently, are 1 or 2,

M is hydrogen or a non-chromophoric cation, and rings B and D, independently, are unsubstituted or substituted by up to three substituents selected from up to two from C$_{1-3}$alkyl and up to two from halogen.

2. A process according to claim 1 which comprises applying a compound of the formula:

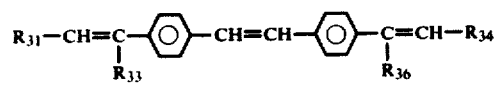

in which

R$_{31}$ and R$_{34}$, independently, signify —CN, —COOR''' or —SO$_2$—Rx, and

R$_{33}$ and R$_{36}$, independently, signify hydrogen or C$_{1-4}$alkyl.

3. A process according to claim 2 which comprises applying a compound of the formula

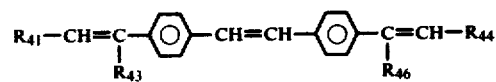

wherein

R$_{41}$ and R$_{44}$, independently, signify —CN, —COOR$^{iv}$or —SO$_2$Rx$^{iv}$, where R$^{iv}$ is methyl or C$_{2-6}$alkyl, unsubstituted or mono-substituted by hydroxy, C$_{1-4}$-alkoxy, C$_{1-4}$alkoxy-C$_{2-6}$alkoxy or C$_{2-6}$hydroxyalkoxy, Rx$^{iv}$ is unsubstituted C$_{1-6}$alkyl or phenyl, unsubstituted or mono-substituted by halogen C$_{1-3}$alkyl or C$_{1-3}$-alkoxy, and R$_{43}$ and R$_{46}$, independently, are hydrogen or methyl.

4. A process according to claim 1 wherein, in the compound of formula I'', Rx is methyl, C$_{2-6}$alkyl, unsubstituted or mono-substituted by C$_{1-4}$alkoxy or C$_{1-4}$alkoxy-C$_{2-6}$alkoxy; phenyl, unsubstituted or mono-substituted by halogen, C$_{1-3}$alkyl or C$_{1-3}$alkoxy; or naphthyl, R' and R'', independently, are hydrogen, methyl, C$_{2-4}$alkyl, unsubstituted or mono-substituted by hydroxy and R''' is methyl or C$_{2-6}$alkyl unsubstituted or mono-substituted by hydroxy, C$_{1-4}$alkoxy, C$_{1-4}$alkoxy-C$_{2-6}$alkoxy or C$_{2-6}$hydroxyalkoxy.

5. A process according to claim 4 wherein Rx is unsubstituted C$_{1-6}$alkyl or phenyl, unsubstituted or mono-substituted by chlorine or methyl, R' and R'' have the same significance and R''' is unsubstituted C$_{1-6}$alkyl.

6. A process according to claim 1 wherein, in the compound of formula I'', R$_{21}$ and R$_{24}$ are cyano.

7. A process according to claim 35 wherein, in the compound of formula I'', R$_{21}$ and R$_{24}$ are —CO$_2$R'''.

8. A process according to claim 6 wherein the compound of formula I'' is

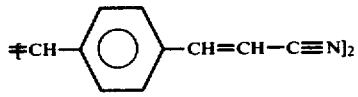

9. A process according to claim 7 wherein the compound of formula I'' is

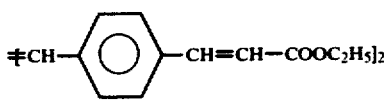

10. A process according to claim 1 wherein the material is polyester, polyamide, polyurethane, polypropylene, cellulose ester or polyacrylonitrile.

11. A process according to claim 10 wherein the compound of formula I'' is applied by exhaust, steeping or padding from an aqueous bath which may also contain a carrier, thickener or dispersing agent and said compound is fixed on the material using saturated steam, high temperature or the thermosol method.

12. A process according to claim 10 wherein the compound of formula I'' is added to a melt or solution of the material to be brightened or by adding said compound to a monomer or prepolymer of the material.

13. A process according to claim 1 wherein the compound of formula I'' is employed in an amount between 0.001 and 0.5% based on the weight of the material.

14. A process according to claim 1 wherein, in the compound of formula I'', M is hydrogen, an alkali metal or alkaline earth metal cation or a cation of the formula R$_p$R$_q$R$_s$NH wherein R$_p$, R$_q$ and R$_s$, independently, are hydrogen, unsubstituted C$_{1-4}$ alkyl or C$_{2-4}$ alkyl mono-substituted by hydroxy.

15. A process according to claim 2 wherein, in the compound of formula I''', M is hydrogen, an alkali metal or alkaline earth metal cation or a cation of the formula R$_p$R$_q$R$_s$NH wherein R$_p$, R$_q$ and R$_s$, independently, are hydrogen, unsubstituted C$_{1-4}$ alkyl or C$_{2-4}$ alkyl mono-substituted by hydroxy.

* * * * *